(12) United States Patent
Tauchi

(10) Patent No.: US 7,045,523 B2
(45) Date of Patent: May 16, 2006

(54) COMBINATION COMPRISING N-{5-[4-(4-METHYL-PIPERAZINO-METHYL)-BENZOYLAMIDO]-2-METHYLPHENYL}-4-(3-PYRIDYL)-2-PYRIMIDINE-AMINE AND TELOMERASE INHIBITOR

(75) Inventor: Tetsuzo Tauchi, Kanagawa (JP)

(73) Assignee: Novartis AG, Basel (CH)

( * ) Notice: Subject to any disclaimer, the term of this patent is extended or adjusted under 35 U.S.C. 154(b) by 20 days.

(21) Appl. No.: 10/272,837

(22) Filed: Oct. 17, 2002

(65) Prior Publication Data

US 2003/0166660 A1 Sep. 4, 2003

(30) Foreign Application Priority Data

Oct. 18, 2001 (GB) .................................... 0125105
Jul. 4, 2002 (GB) .................................... 0215583

(51) Int. Cl.
*A61K 31/506* (2006.01)
*A61K 31/33* (2006.01)

(52) U.S. Cl. .................................... 514/252.18; 514/183
(58) Field of Classification Search ................ 514/183, 514/252.18
See application file for complete search history.

(56) References Cited

FOREIGN PATENT DOCUMENTS

| EP | 0 819 433 A2 | 1/1998 |
|---|---|---|
| EP | 1 123 937 | 8/2001 |
| WO | WO 99/03854 | 1/1999 |
| WO | WO 00/18234 | 4/2000 |
| WO | WO 01/02377 | 1/2001 |

OTHER PUBLICATIONS

Tauchi et al., Oncogene, 22, 5338-5437 (2003).*
Nakajima et al., "Efficacy of SCH66336, The Farnesyl Transferase Inhibitor, in Conjuction with Other Antileukemic Agents Against Glivec-resistant BCR-ABL-positive Cells", *Blood*, vol. 98, No. 11, Pt. 1, p. 575a (2001)—Abstract 2002:209875 BIOSIS.
Shin-ya et al., "Telomestatin, a Novel Telomerase Inhibitor from *Streptomyces anulatus*", *J Am Chem Soc*, vol. 123, pp. 1262-1263 (2001).
Taudi et al., "Activity of a Novel Telomerase Inhibitor, Telomestatin, Against Glivec-resistant BCR-ABL-positive Cells", *Blood*, vol. 98, No. 11, Pt. 1, p. 616a (2001)—Abstract 2002:220199 BIOSIS.

* cited by examiner

*Primary Examiner*—Phyllis G. Spivack
(74) *Attorney, Agent, or Firm*—Oona A. Jackson; Lydia T. McNally; George R. Dohmann

(57) ABSTRACT

A method of treating BCR-ABL positive leukemia in a warm-blooded animal comprising administering the combination of N-{5-[4-(4-methyl-piperazino-methyl)-benzoylamido]-2-methylphenyl}-4-(3-pyridyl)-2-pyrimidine-amine, or a pharmaceutically acceptable salt thereof, and telomestatin is disclosed. The combination may optionally have a pharmaceutically acceptable carrier, and the compounds may be administered for simultaneous, separate or sequential use.

6 Claims, No Drawings

COMBINATION COMPRISING N-{5-[4-(4-METHYL-PIPERAZINO-METHYL)-BENZOYLAMIDO]-2-METHYLPHENYL}-4-(3-PYRIDYL)-2-PYRIMIDINE-AMINE AND TELOMERASE INHIBITOR

The invention relates to a method of treating a warm-blooded animal, especially a human, having a proliferative disease comprising administering to the animal a combination which comprises (a) N-{5-[4-(4-methyl-piperazino-methyl)-benzoylamido]-2-methylphenyl}-4-(3-pyridyl)-2-pyrimidine-amine and (b) at least one telomerase inhibitor, especially as defined herein; a combination comprising (a) and (b) as defined above and optionally at least one pharmaceutically acceptable carrier for simultaneous, separate or sequential use, in particular for the delay of progression or treatment of a proliferative disease, especially a tumor disease and leukemia; a pharmaceutical composition comprising such a combination; the use of such a combination for the preparation of a medicament for the delay of progression or treatment of a proliferative disease, and finally to the use of at least one telomerase inhibitor for the preparation of a medicament for the delay of progression or treatment of an Imatinib-resistant leukemia; and to a commercial package or product comprising such a combination.

The preparation of N-{5-[4-(4-methyl-piperazino-methyl)-benzoylamido]-2-methylphenyl}-4-(3-pyridyl)-2-pyrimidine-amine and the use thereof, especially as an antiproliferative agent, are described in EP-A-0 564 409, which was published on 6 Oct. 1993 and in equivalent applications in numerous other countries. This compound is also known and hereinafter referred to as Imatinib [International Nonproprietary Name].

Telomerase is a DNA polymerase with an endogenous RNA template, on which the nascent telomeric repeats are synthesized. It is known that approximately 85–90% of all human cancers are positive for telomerase, both in cultured tumor cells and primary tumor tissue, whereas most somatic cells appear to lack detectable levels of telomerase. This finding has been extended to a wide range of human tumors (see, for example, Hiyama et al., "Correlating telomerase activity levels with human neuroblastoma outcomes," Nature Medicine, 1:249–255, 1995a.). Therefore, Human telomerase is now considered as a novel and potentially highly selective target for antitumor drug design, and many new promising telomerase inhibitors have been discovered (Anne E. Pitts and David R. Corey[4], "The telomerase challenge—an unusual problem in drug discovery"; Drug Discovery Today 1999, 4:155–161).

Surprisingly, it has been found that the effect in treating a proliferative disease of a combination which comprises (a) Imatinib or pharmaceutically acceptable salts thereof, and (b) at least one telomerase inhibitor is greater than the effects that can be achieved with either type of combination partner alone, i.e. a supra-additive or synergistic effect.

This combination shows especially good results for treating leukemia or Imatinib-resistant leukemia.

Furthermore, it was surprisingly found that telomerase inhibitors are particularly useful for treating leukemia resistant to Imatinib or pharmaceutically acceptable salts thereof and resulted in unexpected strong inhibition of telomerase activity and reduction of telomere length.

Hence, in a first embodiment, the present invention relates to a method of treating a warm-blooded animal having Imatinib-resistant leukemia comprising administering to the animal at least one telomerase inhibitor in a quantity which is therapeutically effective against leukemia, in which method said compounds can also be present in the form of their pharmaceutically acceptable salts.

In a second embodiment, the present invention relates to the use of at least one telomerase inhibitor for the manufacture of a drug useful for treating a warm-blooded animal having I Imatinib-resistant leukemia.

In a third aspect embodiment, the present invention relates to a method of treating a warm-blooded animal having Imatinib-resistant leukemia comprising administering to the animal at least one telomerase inhibitor in a quantity which is therapeutically effective against leukaemia, in which method said compounds can also be present in the form of their pharmaceutically acceptable salts.

Furthermore, the present invention relates to a combination, such as a combined preparation or a pharmaceutical composition, which comprises (a) N-{5-[4-(4-methyl-piperazino-methyl)-benzoylamido]-2-methylphenyl}-4-(3-pyridyl)-2-pyrimidine-amine and (b) at least one telomerase inhibitor, wherein the active ingredients are present in each case in free form or in the form of a pharmaceutically acceptable salt, and optionally at least one pharmaceutically acceptable carrier; for simultaneous, separate or sequential use.

The present invention also concerns a method of treating a warm-blooded animal having a proliferative disease comprising administering to the animal a combination which comprises (a) N-{5-[4-(4-methyl-piperazino-methyl)-benzoylamido]-2-methylphenyl}-4-(3-pyridyl)-2-pyrimidine-amine and (b) at least one telomerase inhibitor, in a quantity which is jointly therapeutically effective against a proliferative disease and in which the compounds can also be present in the form of their pharmaceutically acceptable salts.

Furthermore, the present invention pertains to a pharmaceutical composition comprising a quantity, which is jointly therapeutically effective against a proliferative disease of a combination as defined herein and at least one pharmaceutically acceptable carrier.

In the herein disclosed methods, combinations, compositions or uses, the combination partners (a) and (b) are preferably administered in synergistically effective amounts.

The term "proliferative disease" includes malignant and non-malignant proliferative diseases, e.g. atherosclerosis, carcinomas and leukemia, tumors, thrombosis, psoriasis, restenosis, sclerodermitis and fibrosis.

The term "tumor" as used herein includes, but is not limited to breast cancer, melanoma, epidermoid cancer, cancer of the colon and generally the GI tract, lung cancer, in particular small-cell lung cancer, and non-small-cell lung cancer, head and neck cancer, genitourinary cancer, e.g. cervical, uterine, ovarian, testicles, prostate or bladder cancer; Hodgkin's disease or Kaposi's sarcoma. The combinations of the present invention inhibit the growth of liquid tumors and, in particular, solid tumors. Furthermore, depending on the tumor type and the particular combination used a decrease of the tumor volume can be obtained. The combinations disclosed herein are also suited to prevent the metastatic spread of tumors and the growth or development of micrometastases. The combinations disclosed herein are in particular suitable for the treatment of poor prognosis patients, e.g. such poor prognosis patients having non-small-cell lung cancer.

The term "leukemia" as used herein includes, but is not limited to, chronic myelogenous leukemia (CML) and acute lymphocyte leukemia (ALL), especially Philadelphia-chromosome positive acute lymphocyte leukemia (Ph+ ALL) as well as Imatinib-resistant leukemia. Preferably, the variant of leukemia to be treated by the methods disclosed herein is CML.

The term "Imatinib-resistant leukemia" as used herein defines especially a leukemia in which Imatinib shows a reduction of its therapeutic effectiveness or the relive of its therapeutic activity for the treatment of leukemia.

The term "a combined preparation", as used herein defines especially a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b). The ratio of the total amounts of the combination partner (a) to the combination partner (b) to be administered in the combined preparation can be varied, e.g. in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular a synergism, e.g. a more than additive effect, additional advantageous effects, less side effects, a combined therapeutical effect in a non-effective dosage of one or both of the combination partners (a) and (b), and very preferably a strong synergism of the combination partners (a) and (b).

The term "delay of progression" as used herein means administration of the combination to patients being in a pre-stage or in an early phase of the disease to be treated, in which patients for example a pre-form of the corresponding disease is diagnosed or which patients are in a condition, e.g. during a medical treatment or a condition resulting from an accident, under which it is likely that a corresponding disease will develop.

It will be understood that references to the combination partners (a) and (b) are meant to also include the pharmaceutically acceptable salts. If this combination partners (a) and (b) have, for example, at least one basic center, they can form acid addition salts. Corresponding acid addition salts can also be formed having, if desired, an additionally present basic center. The combination partners (a) and (b) having an acid group (for example COOH) can also form salts with bases. The combination partner (a) or (b) or a pharmaceutically acceptable salt thereof may also be used in form of a hydrate or include other solvents used for crystallization. N-{5-[4-(4-methyl-piperazino-methyl)-benzoylamido]-2-methylphenyl}-4-(3-pyridyl)-2-pyrimidine-amine, i.e. combination partner (a), is preferably used in the present invention in the form of its monomesylate salt. Depending on the chemical structure of the telomerase inhibitor, a salt form thereof may not exist.

The combination partner (a) can be prepared and administered as described in WO 99/03854, especially the monomesylate salt of N-{5-[4-(4-methyl-piperazino-methyl)-benzoylamido]-2-methylphenyl}-4-(3-pyridyl)-2-pyrimidine-amine can be formulated as described in Examples 4 and 6 of WO 99/03854.

The term "telomerase inhibitior" is simply meant a reagent, drug or chemical which is able to decrease the activity of the telomerase enzyme in vitro or in vivo. Such inhibitors can be readily identified using standard screening protocols in which a cellular extract or other preparation having telomerase activity is placed in contact with a potential inhibitor, and the level of telomerase activity measured in the presence or absence of the inhibitor, or in the presence of varying amounts of inhibitor. In this way, not only can useful inhibitors be identified, but the optimum level of such an inhibitor can be determined in vitro for further testing in vivo. Examples of inhibitors are Telomestatin (J. Am. Chm. Soc. 2001, 123, 1262–1263), Dimethyl sulfoxide, protein kinase C inhibitors (bisindolylmaleimide I and H-7), cisplatin, antisense c-myc oligonucleotides (Kohtaro Fujimoto, Morinobu Takahashi, Biochem Biophys Res Commun "*Telomerase Activity in Human Leukemic Cell Lines Is Inhibited by Antisense Pentadecadeoxynucleotides Targeted against c-myc mRNA*", 1997 December, 241:775–81), G-quadruplex structures described in WO 01/402377, selective DNA triplex interactive compounds (Fox et al., "A molecular anchor for stabilizing triple-helical DNA," Proc; Haq et al., "Molecular anchoring of duplex and triplex DNA by disubstituted anthracene-9/10-diones", J. Am. Chem. Soc., 118:10693–10701, 1996), 2,6-diamido-anthraquinones reported as DNA-interactive agents (Collier and Neidle, "Synthesis, molecular modeling, DNA binding, and antitumor properties of some substituted amidoanthraquinones," Med. Chem., 31:847–857, 1988; Agbandje et al., "Anthracene-9,10-diones as potential anticancer agents. Synthesis, DNA binding, and biological studies on a series of 2,6-disubstituted derivatives," Med. Chem., 35:1418–1429, 1992.), compounds as described in WO 99/65845 or carbocyanine dye, 3,3'-diethyloxadicarbocyanine (DODC,), reported to bind dimeric hairpin G-quadruplex structures (Chen et al., "Spectroscopic recognition of guanine dimeric hairpin quadruplexes by a carbocyanine dye," Proc. Natl. Acad. Sci. USA, 93:2635–2639, 1996.) or thiazolidinedione compounds. Representative known thiazolidinedione compounds include the glitazones, such as, for example, troglitazone (also known as CS-045 (Sankyo) and CI-991 (Park-Davis)), pioglitazone (also known as AD-4833 and U-72107E), rosiglitazone (also known as BRL49653), englitazone (also known as CP-68,722), and ciglitazone or compounds described in WO 01/02377. Anne E. Pitts and David R. Corey reported other inhibitors of human telomerase activity such as Phosphorothioate DNA, Ribozyme, Oligonucleotide with 2'–5' A linkage, Tea catechins, Nucleoside derivatives, Perylenetetracarboxylic diimide, Cationic porphyrin, Anthraquinone derivatives, Phosphodiester DNA oligos, Peptide nucleic acid, antisense RNA (Anne E. Pitts and David R. Corey, "*The telomerase challenge—an unusual problem in drug discovery*"; Drug Discovery Today 1999, 4:155–161).

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

A combination which comprises (a) N-{5-[4-(4-methyl-piperazino-methyl)-benzoylamido]-2-methylphenyl}-4-(3-pyridyl)-2-pyrimidine-amine and (b) at least one telomerase inhibitor, in which the active ingredients are present in each case in free form or in the form of a pharmaceutically acceptable salt and optionally at least one pharmaceutically acceptable carrier, will be referred to hereinafter as a COMBINATION OF THE INVENTION. Depending on the structure of the telomerase inhibitor, a salt form may impossible.

The nature of proliferative diseases like solid tumor diseases is multifactorial. Under certain circumstances, drugs with different mechanisms of action may be combined. However, just considering any combination of drugs having different mode of action does not necessarily lead to combinations with advantageous effects.

The utility of the invention for the treatment of proliferative diseases such as leukemia is demonstrated, by the ability of the COMBINATION OF THE INVENTION or a telomerase inhibitor taken alone to inhibit the transformation of BCR-ABL positive OM9;22 cells or Imatinib-resistant BCR-ABL positive OM9;22R cells.

In the present study, the clinical candidate telomerase inhibitor, telomestatin (J. Am. Chem. Soc. 123; 1262, 2001), was characterized for its ability to inhibit BCR-ABL transformation. When tested against BCR-ABL positive OM9;22 cells or Imatinib-resistant BCR-ABL positive OM9;22R cells, a human leukemia cell line derived from Ph positive acute lymphoblastic leukemia patient, treatment of telomestatin resulted in unexpected strong inhibition of telomerase activity and reduction of telomere length. Treatment of telomestatin potently inhibited soft agar colony formation, slowed proliferation within 2 weeks. Cell cycle analysis of OM9;22 or OM9;22R cells treated with telomestatin revealed G1/S blockage. Telomestatin induced phosphorylation of p95/NBS protein, essential for the cellular response to DNA damage, and increased the expression of p21CIP1 and p27KIP1 in OM9;22R cells. In addition, we examined the impact of telomestatin on human normal hematopoietic progenitor cells by a clonogenic assay, and we observed significantly less sensitive at the concentrations 10 times higher than those that completely inhibited colonies from OM9;22R cells. These results demonstrate that disruption of telomere maintenance by telomestatin alters the chemotherapeutic profile of Imatinib-resistant BCR-ABL transformed cells, and point the combined use of Imatinib and telomestatin as an effective therapeutic approach of Ph positive leukemias.

The combination of telomestatin with Imatinib or daunorubicine showed supra-additive or synergistic effects in soft agar colony formation, whereas, the combination of telomestatin with cytosine arabinoside or stoposide did not show any synergistic effect and even no additive effect.

All the more surprising is the experimental finding that the administration of a COMBINATION OF THE INVENTION, especially comprising telomestatine as combination partner (b), results not only in a beneficial effect, especially a supra-additive or synergistic therapeutic effect, e.g. with regard to slowing down the formation of soft agar colonies, but also in further beneficial effects, e.g. less side-effects, an improved quality of life and a decreased mortality and morbidity, compared to a monotherapy applying only one of the pharmaceutically active ingredients used in the COMBINATION OF THE INVENTION, in particular in the treatment of proliferative diseases refractory to other chemotherapeutics known as anti-cancer agents. In particular, an unexpected increased up-take of the combination partner (b) in tumor tissue, tumor cells or human leukemia cells (i.e. BCR-ABL) is supposed, when applied in combination with combination partner (a).

A further benefit is that lower doses of the active ingredients of the COMBINATION OF THE INVENTION can be used, for example, that the dosages need not only often be smaller but are also applied less frequently, or can be used in order to diminish the incidence of side-effects. This is in accordance with the desires and requirements of the patients to be treated. This supra-additive interaction is not associated with a similar increase in adverse effects potential.

It can be shown by established test models and in particular those test models described herein that a COMBINATION OF THE INVENTION results in a more effective delay of progression or treatment of a proliferative disease compared to the effects observed with the single combination partners. The person skilled in the pertinent art is fully enabled to select a relevant test model to prove the hereinbefore and hereinafter mentioned therapeutic indications and beneficial effects. The pharmacological activity of a COMBINATION OF THE INVENTION may, for example, be demonstrated in a clinical study or in a test procedure as essentially described hereinafter.

Suitable clinical studies are, for example, open label non-randomized, dose escalation studies in patients with advanced proliferative diseases. Such studies can in particular prove the synergism of the active ingredients of the COMBINATIONS OF THE INVENTION. The beneficial effects on proliferative diseases can be determined directly through the results of these studies or by changes in the study design which are known as such to a person skilled in the art. Such studies are, in particular, suitable to compare the effects of a monotherapy using the active ingredients and a COMBINATION OF THE INVENTION. Preferably, the combination partner (a) is administered with a fixed dose and the dose of the combination partner (b) is escalated until the Maximum Tolerated Dosage is reached. In a preferred embodiment of the study, each patient receives daily doses of the combination partner (a).

The efficacy of the treatment can be determined in such studies, e.g., after 18 or 24 weeks by radiologic evaluation of the tumors every 6 weeks.

Alternatively, a placebo-controlled, double blind study can be used in order to prove the benefits of the COMBINATION OF THE INVENTION mentioned herein.

The COMBINATION OF THE INVENTION can also be applied in combination with surgical intervention, mild prolonged whole body hyperthermia and/or irradiation therapy.

In a preferred embodiment of the invention the telomerase inhibitor is telomestatin as described in the European patent application No. 1 123 937 filed in Oct. 20, 1999, or by K. Shin-ya et al. (J. Am. Chem. Soc. 2001, 123, 1262–1263).

The COMBINATION OF THE INVENTION can be a combined preparation or a pharmaceutical composition.

It is one objective of this invention to provide a pharmaceutical composition comprising a quantity, which is jointly therapeutically effective against a proliferative disease comprising the COMBINATION OF THE INVENTION. In this composition, the combination partners (a) and (b) can be administered together, one after the other or separately in one combined unit dosage form or in two separate unit dosage forms. The unit dosage form may also be a fixed combination.

The pharmaceutical compositions for separate administration of the combination partners (a) and (b) and for the administration in a fixed combination, i.e. single galenical compositions comprising at least two combination partners (a) and (b), according to the invention can be prepared in a manner known per se and are those suitable for enteral, such as oral or rectal, and parenteral administration to mammals (warm-blooded animals), including man, comprising a therapeutically effective amount of at least one pharmacologically active combination partner alone or in combination with one or more pharmaceutically acceptable carries, especially suitable for enteral or parenteral application.

Novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partner of the COMBINATION OF THE INVENTION may be administered simultaneously or sequentially and in any order, and the components may be administered separately or as a fixed combination. For example, the method of delay of progression or treatment of a proliferative disease according to the invention may comprise (i) administration of the combination partner (a) in free or pharmaceutically acceptable salt form and (ii) administration of a combination partner (b) in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners of the COMBINATION OF THE INVENTION can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimes of simultaneous or alternating treatment and the term "administering" is to be interpreted accordingly.

An example of sequential administration could be a first administration of N-{5-[4-(4-methyl-piperazino-methyl)-benzoylamido]-2-methylphenyl}-4-(3-pyridyl)-2-pyrimidine-amine until a resistance to the therapy is observed, followed by the administration of a telomerase inhibitor taken alone or in combination with Imatinib.

The effective dosage of each of the combination partners employed in the COMBINATION OF THE INVENTION may vary depending on the particular compound or pharmaceutical composition employed, the mode of administration, the condition being treated, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites.

N-{5-[4-(4-methyl-piperazino-methyl)-benzoylamido]-2-methylphenyl}-4-(3-pyridyl)-2-pyrimidine-amine monomesylate, is preferably administered to a human in a dosage in the range of about 2.5 to 850 mg/day, more preferably 5 to 600 mg/day and most preferably 20 to 300 mg/day. Unless stated otherwise herein, the compound is preferably administered from one to four times per day, more preferably once daily.

Furthermore, the present invention pertains to the use of a COMBINATION OF THE INVENTION for the delay of progression or treatment of a proliferative disease and to the use of a COMBINATION OF THE INVENTION for the preparation of a medicament for the delay of progression or treatment of a proliferative disease.

Preferably, the proliferative disease is leukemia, Imatinib-resistant leukemia and tumors.

Moreover, the present invention provides a commercial package comprising a COMBINATION OF THE INVENTION, together with instructions for simultaneous, separate or sequential use thereof in the delay of progression or treatment of a proliferative disease.

The following Example illustrates the invention described above, but is not, however, intended to limit the scope of the invention in any way. The beneficial effects of the COMBINATION OF THE INVENTION (i.e. good therapeutic margin, less side effects, synergistic therapeutic effect and other advantages mentioned herein), can also be determined by other test models known as such to the person skilled in the pertinent art. The synergistic therapeutic effect, may for example, be demonstrated in a clinical study or in the test procedure as essentially described hereinafter.

Materials and Methods:

Antibodies and Reagents: Anti-ATM Ab (K-19), anti-Chk2 Ab (H-300), anti-NBS1 mAb (N-19), anti-phospho-NBS1 Ab (Ser343), anti-p21$^{CIP1}$ Ab (F-15), anti-p27$^{KIP1}$ Ab (F-8), anti-p15$^{INK4B}$ Ab (K-18), and anti-p16$^{Ink4A}$ Ab (H-156) were purchased from Santa Cruz Biotechnology, Inc. (Santa Cruz, Calif.). Imatinib was kindly provided by Novartis Inc. (Basel, Switzerland). Daunorubicin (DNR), cytosine arabinoside (Ara C), and etoposide (VP-16) were obtained from Sigma (St Louis, Mo.). Telomestatin was purified as previously described (Shin-ya et al., 2001).

Cells and cell culture: The Ph-positive acute lymphoblastic cell line OM9;22 has been described previously (Ohyashiki et al., 1993). K562 cells were obtained from the American Type Culture Collection (Rockville, Md.). These cell lines were cultured in McCoy's 5A modified medium (Life Technology, Inc.) supplemented with 10% fetal calf serum (Hyclone Laboratories, Logan, Utah).

Generation of stable clones expressing DN-hTERT mutants. pBABE-DN-hTERT was a gift from Dr. Robert Weinberg (Massachusetts Institute of Technology). OM9;22 cells were transfected with the expression vector pBABE-puro-DN-hTERT by electroporation. Beginning 48 hours after electroporation, cells were selected with 2 μg/ml of puromycin and cloned by limiting dilution. PD 0 was defined as the time at which cultures reached confluence in 10-cm culture dishes.

Telomerase assay and measurement of TRF. Telomerase activity was examined by a telomere repeat amplification protocol (TRAP) assay using a TRAP$_{EzE}$ telomerase detection kit (Oncor, Gaithersburg, Md.). The PCR products were subjected to 12% acrylamide denaturing electrophoresis in an automated laser fluorescence DNA sequencer II (Pharmacia LKB Biotechnology, AB) and analyzed by the Fragment Manager program (Pharmacia LKB Biotechnology, AB). Activity in the extract-based PCR TRAP assay was detected as a periodic 6-bp peak of telomerase products and, in each sample, relative telomerase activity was calculated semiquantitatively in comparison with a 36-bp internal standard. To measure TRF, genomic DNA was digested with the restriction enzymes Hinfl and Rsal, fractionated on 0.7% agarose gels and transferred onto nylon membranes. Hybridization was performed by using the Telo TTAGGG telomere length assay kit (Roche Molecular Biochemicals, Mannheim, Germany).

Apoptosis assay. The incidence of apoptosis was determined by flow cytometric analysis with the FITC-conjugated APO2.7 monoclonal antibody (clone 2.7), which was raised against the 38 kDa mitochondrial membrane protein (7A6 antigen) and is expressed by cells undergoing apoptosis (Nakajima et al., 2001).

Fluorescence in situ hybridization and quantitative image analysis. Individual telomere length was analysed by quantitative fluorescence in situ hybridization (Q-FISH) as described previously (Martens et al., 1998). Digital images of metaphase spreads were recorded with a digital camera (Sensys, Photometrics) on a Zeiss Axioplan II fluorescence microscope using the Vysis workstation QUIPS. Telomere profiles were analysed by use of the TFL-TELO software (Poon et al., 1999). Telomere fluorescence intensity values were expressed in arbitrary units.

Immunoblotting and Immunoprecipitation. Immunoblotting and immunoprecipitation were performed as described previously (Tauchi et al., 1994). For immune complex kinase assays, immunoprecipitated proteins were incubated with 30 μl of kinase buffer (50 mM HEPES, pH 8.0, 10 mM $MnCl_2$, 2.5 mM EDTA, 1 mM dithiothreitol, 10 mM ATP and 30 mCi of $[\gamma-^{32}P]ATP$ at 30° C. for 30 min. The reaction products were separated by SDS-PAGE, and transferred to the membranes for autoradiography.

Statistical analysis. Comparisons between groups were analyzed by the Mann-Whitney U test. Values of $P<0.05$ were considered to indicate statistical significance. The statistical tests were performed using the Microsoft Word Excel (Brain Power Inc, Calabashes, Calif.) software package for the Macintosh personal computer.

The utility of the invention for the treatment of proliferative disease such as leukemia can also be demonstrated, e.g., in the proliferation test using bcr-Abl transfected 32D cells as follows:

Bcr-Abl-transfected 32D cells (32D pGD p210 Bcr-Abl; Bazzoni, G.; et al. J. Clin. Invest. (1996), 98(2), 521–528) are cultured in RPMI 1640 (BioConcept, Allschwil, Switzerland; cat. No.: 1-41F01), 10% fetal calf serum, 2 mM glutamine. 10000 cells in 50 μL per well are seeded into flat bottom 96 well tissue culture plates. Complete medium alone (for controls) or serial threefold dilutions of compounds are added in triplicates to a final volume of 100 μL and the cells are incubated at 37° C., 5% $CO_2$ for 65 to 72 h. The cell proliferation reagent WST-1 (Roche Diagnostics GmbH; cat.no.: 1 664 807) is added at 10 μL per well followed by 2 h incubation at 37° C. Colour development, depending on the amount of living cells, is measured at 440 nm. The effect for each compound or combination is calculated as percent inhibition of the value ($OD_{440}$) obtained for the control cells (100%) and plotted against the compound concentrations. The $IC_{50}$s are calculated from the dose response curves by graphic extrapolation.

Compounds inhibiting the growth of 32D-Bcr-Abl cells can be further tested on IL-3 dependent 32D wt cells to prove the specificity of the compounds for the bcr-Abl kinase and to exclude compound toxicity.

Results

Effects of telomestatin on cell proliferation. We characterize the growth properties of telomestatin-treated cells. The growth kinetics of telomestatin-treated cells initially did not differ from those of untreated control cells, regardless of the cell line used. K562 cell cultures in the absence or presence of 2 μM of telomestatin exhibit no or only minor differences in proliferation during 20 days of treatment. However, after 30 days, telomestatin-treated K562 cells show an almost complete inhibition of proliferation. Telomestatin-treated OM9;22 or OM9;22R cells also cease to proliferate after 15 days. Telomestatin-treated cells show distinctive morphological features associated with apoptosis. In a further study, we can characterize the ability of telomestatin to inhibit BCR-ABL transformation. When tested against Imatinib-resistant BCR-ABL positive OM9; 22R cells, a human leukemia cell line derived from Ph positive acute lymphoblastic leukemia patient, treatment of telomestatin results in unexpected strong inhibition of telomerase activity and reduction of telomere length. Treatment of telomestatin potently inhibite soft agar colony formation and slows proliferation within 2 weeks.

Cell cycle analysis of OM9;22R cells treated with telomestatin reveal G1/S blockage. Telomestatin induces phosphorylation of p95/NBS protein, essential for the cellular response to DNA damage, and increases the expression of p21CIP1 and p27KIP1 in OM9;22R cells. In addition, we can examine the impact of telomestatin on human normal hematopoietic progenitor cells by a clonogenic assay, and we observe significantly less sensitive at the concentrations 10 times higher than those that completely inhibit colonies from OM9;22R cells. These results demonstrate that disruption of telomere maintenance by telomestatin alters the chemotherapeutic profile of Imatinib-resistant BCR-ABL transformed cells, and point the combined use of Imatinib and telomestatin as an effective therapeutic approach of Ph positive leukemias.

Enhancement of apoptosis in telomestatin-treated K562 cells by chemotherapeutic agents. Since early passaged telomestatin-treated K562 cells did not show induction of apoptosis, we decided to examine the impact of telomerase inhibition on chemotherapeutic responses (Table A). Mechanistically distinct classes of reagents are selected for analysis, including imatinib, daunorubicin (DNR), mitoxantrone (MIT), and vincristine (VCR). To assess the effects of telomerase inhibition in modulating responses to these reagents, experiments focused on early passaged telomestatin-treated K562 cells (PD10). In this series of experiments, K562 cells are cultured with telomestatin for 10 days, subsequently the telomestatin-treated K562 cells are incubated with the agents for 48 hours, and the incidence of apoptosis is determined by flow cytometric analysis with APO2.7 mAb (Table A). Apo2.7 is the apoptosis index. Higher score means that apoptosis is induced more powerfully.

TABLE A

| APO2.7 (%) | 0 nM | 10 nM | 50 nM | 100 nM | 500 nM | 1000 nM |
|---|---|---|---|---|---|---|
| Imatinib (control) | 8 | | | 9 | 12 | 28 |
| Imatinib + Telom 2 μM | 8 | | | 22 | 62 | 90 |
| DNR (control) | 10 | 11 | 23 | 36 | 53 | |
| DNR + Telomest 2 μM | 10 | 32 | 50 | 70 | 85 | |
| MIT (control) | 9 | 10 | 12 | 17 | 29 | 38 |
| MIT + Telomest 2 μM | 9 | 10 | 11 | 33 | 47 | 62 |
| VCR (control) | 5 | 12 | 18 | 24 | 29 | 34 |
| VCR + Telomest 2 μM | 5 | 18 | 32 | 44 | 57 | 74 |

The telomestatin-treated K562 cells show enhanced induction of apoptosis compared with control cells after exposure to imatinib, DNR, MIT and VCR (Table A), whereas significant chemosensitivity is not observed in cells exposed to etoposide (VP-16), 6-mercaptopurine (6-MP), methotrexate (MTX), cytosine arabimoside and stoposide (data not shown). These results, demonstrating enhanced sensitivity to some classes of chemotherapeutic agents, imply cytotoxic synergy between telomere dysfunction and these agents. Thus synergistic effects of combinations comprising telomestatin with imatinib, DNR, MIT and VCR have been shown.

We conclude that telomerase inhibitors combined with use of imatinib and other chemotherapeutic agents may be very useful for the treatment of BCR-ABL-positive leukemia.

What is claimed is:

1. A method of treating BCR-ABL positive leukemia in a warm-blooded animal comprising administering to the warm-blooded animal a therapeutically effective amount of a compound comprising (a) N-{5-[4-(4-methyl-piperazino-methyl)-benzoylamido]-2-methylphenyl}-4-(3-pyridyl)-2-pyrimidine-amine or a pharmaceutically acceptable salt thereof and (b) telomestatin or a pharmaceutically acceptable salt thereof.

2. The method according to claim 1, wherein (a) and (b) are administered in synergistically effective amounts.

3. A combination comprising (a) N-{5-[4-(4-methyl-piperazino-methyl)-benzoylamido]-2-methylphenyl}-4-(3-pyridyl)-2-pyrimidine-amine or a pharmaceutically acceptable salt thereof and (b) telomestatin or a pharmaceutically acceptable salt thereof for simultaneous, separate or sequential use.

4. The combination according to claim 3, wherein N-{5-[4-(4-methyl-piperazino-methyl)-benzoylamido]-2-methylphenyl}-4-(3-pyridyl)-2-pyrimidine-amine is in the form of its monomethanesulfonate salt.

5. A pharmaceutical composition comprising the combination according to claim 3 and at least one pharmaceutically acceptable carrier.

6. A commercial package comprising the combination according to claim 3, together with instructions for simultaneous, separate or sequential use thereof.

* * * * *

UNITED STATES PATENT AND TRADEMARK OFFICE
CERTIFICATE OF CORRECTION

PATENT NO. : 7,045,523 B2 Page 1 of 1
APPLICATION NO. : 10/272837
DATED : May 16, 2006
INVENTOR(S) : Tetsuzo Tauchi It is certified that error appears in the above-identified patent and that said Letters Patent is hereby corrected as shown below:

On the title page

Item (54) should read:

-- (54) COMBINATION COMPRISING N-{5-[4-(4-METHYL-PIPERAZINO-METHYL)-BENZOYLAMIDO]-2-METHYLPHENYL}-4-(3-PYRIDYL)-2-PYRIMIDINE-AMINE AND TELOMESTATIN --.

Signed and Sealed this

Twelfth Day of December, 2006

JON W. DUDAS
*Director of the United States Patent and Trademark Office*